United States Patent
Matsuda et al.

(10) Patent No.: US 7,204,032 B2
(45) Date of Patent: Apr. 17, 2007

(54) PRODUCTION METHOD OF THREE-DIMENSIONAL SHAPE DATA OF DENTAL PROSTHESIS

(75) Inventors: Yoshinori Matsuda, Itabashi-ku (JP); Yuki Sakamoto, Itabashi-ku (JP); Yoshinori Ebihara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 11/261,534

(22) Filed: Oct. 31, 2005

(65) Prior Publication Data

US 2006/0090361 A1 May 4, 2006

(30) Foreign Application Priority Data

Oct. 29, 2004 (JP) .............................. 2004-315530

(51) Int. Cl.
*G01B 5/004* (2006.01)
*A61C 19/04* (2006.01)
(52) U.S. Cl. .......................................... 33/503; 33/513
(58) Field of Classification Search ................ 33/1 M, 33/503, 512, 513, 514, 551, 553, 554, 556; 433/72; 602/587; 702/155, 167
See application file for complete search history.

(56) References Cited

U.S. PATENT DOCUMENTS

| | | | | | |
|---|---|---|---|---|---|
| 4,997,369 | A | * | 3/1991 | Shafir | ............................. 33/513 |
| 5,121,550 | A | * | 6/1992 | Wood et al. | ................... 33/551 |
| 5,467,289 | A | * | 11/1995 | Abe et al. | .................... 702/167 |
| 5,758,429 | A | * | 6/1998 | Farzan et al. | .................. 33/503 |
| 5,924,862 | A | * | 7/1999 | White | .......................... 433/72 |
| 6,640,150 | B1 | | 10/2003 | Persson et al. | |
| 2005/0266372 | A1 | * | 12/2005 | Chu | ........................... 433/72 |
| 2006/0037208 | A1 | * | 2/2006 | McMurtry | ................... 33/554 |
| 2006/0101660 | A1 | * | 5/2006 | Takanashi | .................... 33/503 |

FOREIGN PATENT DOCUMENTS

| | | |
|---|---|---|
| EP | 0 600 800 A1 | 6/1994 |
| JP | 5-332731 | 12/1993 |
| JP | 7-181022 | 7/1995 |
| JP | 2002-257511 | 9/2002 |

\* cited by examiner

*Primary Examiner*—G. Bradley Bennett
(74) *Attorney, Agent, or Firm*—Oblon, Spivak, McClelland, Maier & Neustadt, P.C.

(57) ABSTRACT

To provide a production method of three-dimensional shape data of a part other than an engaging portion by a three-dimensional measuring device, the engaging portion has an engaging part in a cross sectional shape other than a rotary body and is projected and/or recessed on a jawbone side, a measured object mounting tool 2 comprises a cylindrical part 2a, a mounting part 2b and a placing part 2c, the mounting part 2b positions a prolonged line of an axis of the cylindrical part 2a in the engaging part 3aa, the placing part 2c aligns a pre-specified direction of the mounting part 2b with a specified providing direction of the placing table 1b, the center axis of the cylindrical part 2a is aligned with Z axis, and the model of the dental prosthesis 3 is rotated around Z axis on the basis of the specified providing direction of the placing table 1b.

16 Claims, 5 Drawing Sheets

PRODUCTION METHOD OF THREE-DIMENSIONAL SHAPE DATA OF DENTAL PROSTHESIS

BACKGROUND OF THE INVENTION

1. Field of the Invention

The present invention relates to a production method of three-dimensional data of a dental prosthesis for cutting a block for cutting the dental prosthesis by an automatic cutting machine by using a three-dimensional measuring device so as to have the same shape as a measured object.

2. Description of the Conventional Art

As a general production method of the dental prosthesis such as an inlay, a crown, a bridge or the like, the following methods have been widely known. A method comprises casting of a metallic material by a lost wax casting method, to thereby produce the dental prosthesis. Another method comprises building up of a ceramics material on a refractory model, and baking of it in a vacuum electric furnace, to thereby produce the dental prosthesis for the purpose of aesthetic appreciation, such as a ceramic inlay, an all ceramic crown or the like.

However, as for the work for producing the dental prosthesis by the conventional method such as the lost wax casting method, the baking by the vacuum electric furnace or the like, almost all processes are carried out by a manual labor by a dental technician. Further, the process by the manual labor is remarkably fine and complicated. Thus, such the process takes remarkable time and effort, and the quality of the dental prosthesis is influenced by the level of a skill of the dental technician.

Then, as a method for producing much more dental prosthesis having even quality in a short time without depending on the manual labor of the dental technician, a dental CAD/CAM system for producing the dental prosthesis has been developed in recent years. In this technique, the dental prosthesis is produced by the steps of producing the three-dimensional shape data of the dental prosthesis such as the inlay, the crown, the bridge or the like by using a three-dimensional measuring device, a computer or the like, and cutting the block for cutting of the dental prosthesis by an automatic cutting machine on the basis of the obtained three-dimensional shape data of the dental prosthesis.

As such the three-dimensional measuring device in the dental CAD/CAM system, for example, a device comprising a holding base for the measured object, a rotating jig for the holding base, a changing jig for a holding base rotating shaft, a changing jig for a holding base position, and a laser measuring part, is used (for example, referring to Japanese Patent Application Laid Open No. 5-332731).

Such the device is effective when a small measured object is measured to thereby produce the three-dimensional shape data of the dental prosthesis. The small measured object is a small type dental prosthesis applied to only one tooth, such as the inlay, the crown or the like. However, the device has a structure where only the holding base of the measured object is rotated by the rotating jig, so that there is a problem that the large size measured object cannot be measured. The large size measured object is a model of a large-sized type dental prosthesis applied to a plurality of teeth, such as the bridge or the like, or a gypsum model of a plurality of remaining teeth, or the like.

Then, for example, the following three-dimensional devices capable of measuring the large size measured object to thereby produce the three-dimensional shape data, has been developed, where the large size measured object is the model of the large size dental prosthesis applied to the plurality of teeth, such as the bridge or the like, or the gypsum model of the plurality of remaining teeth, or the like. One device comprises a body base, a rotary stage, an X and Y stage, a drive control means, a measured object holding means, an R stage, a first laser displacement gauge, a Z stage, and a second laser displacement gauge (for example, referring to Japanese Patent Application Laid Open No. 7-181022). In this device, the X and Y stages are movable in the specified horizontal direction X and the horizontal direction Y orthogonal to the direction x independently from the rotation of the rotary stage, and has a fitting part for fitting with another member. The drive control means controls the drives of the rotary stage and the X and Y stages respectively. The measured object holding means has a part to be fitted with a fitting part of the X and Y stages, and a fitting part for fitting with the measured object. The R stage is movable in the diameter direction of the rotary stage. The first laser displacement gauge provided at the under face of the R stage so as to make its optical axis to be parallel to a rotating shaft of the rotary stage. The Z stage is movable in the direction parallel to the rotating shaft. The second laser displacement gauge is provided at the side face of the Z stage so as to cross orthogonally with the rotating shaft. Another device comprises an Xθ and Yθ stage, a first drive means, an X and Y stage, a fixing tool, a second drive means, an optical probe, and a computer (for example, referring to Japanese Patent Application Laid Open No. 2002-257511). In this device, the Xθ and Yθ stages are rotated in Xθ and Yθ directions. The first drive means finely drives these Xθ and Yθ stage in respective directions. The X and Y stage moves in X and Y directions on the Xθ and Yθ stage. The fixing tool fixes the measured object having the spherical face on the X and Y stage. The second drive means finely drives the X and Y stage in respective directions. The optical probe measures the three-dimensional coordinate values of the face of the measured object. The computer controls the first drive means and the optical probe, and arithmetically processes signals.

Such the devices can measure the large size measured object and make the three-dimensional shape data, where the object is the model of the large size dental prosthesis applied to the plurality of teeth, such as the bridge or the like, or the gypsum model of the plurality of remaining teeth, or the like. However, the device is complicated itself, difficult to be controlled, and at high production cost. Further, since the former device has two laser displacement gauges, there are problems that the maintenance and production costs are high.

Then, the three-dimensional measuring device capable of measuring from the small measured object to the large measured object, and decreasing the production and maintenance costs by having one laser sensor for measuring the shape of the measured object, is developed, where the small measured object is the model of the small type dental prosthesis applied to small number of teeth, such as the inlay, the crown or the like, and the large measured object is the model of the large type dental prosthesis applied to large number of teeth, such as the bridge or the like, or the gypsum model of large number of remaining teeth, or the like. This device comprises a rotary table, an XY table, and a measuring part for measuring the three-dimensional coordinates of the shape of the measured object. In this device, the rotary table has a rotating shaft, with an axis being Z axis. The XY table is arranged on the rotary table, movable in the X axial direction and the Y axial direction, and has a placing table fixed on the upper part thereof, where the placing table is for providing a measured object mounting tool thereon in a specified direction. The measuring part measures the three-dimensional coordinates of the measured object shape mounted to the measured object mounting tool on the placing table by one laser sensor, which at least can rotationally move on one plane containing the Z axis around a desired point on the Z axis.

As a method for measuring the model of the dental prosthesis such as the inlay, the crown, the bridge or the like to thereby produce the three-dimensional shape data by such the device, for example, the following methods have been carried out. One method comprises, providing the model of the dental prosthesis on the placing table in the three-dimensional measuring device so as to direct its jawbone side to the side direction, measuring it, and thereby making the three-dimensional shape data. The model of the dental prosthesis is formed with a wax, a synthetic resin or the like. The jawbone side is to be engaged with an abutment tooth. (Hereinafter, this method is referred to as "the former production method of the three-dimensional shape data".) Another method comprises, providing the model of the dental prosthesis on the placing table in the three-dimensional measuring device in the state of the model being engaged with a model of an abutment tooth or a model of an alveolar ridge, measuring the model of the dental prosthesis, removing then the model of the dental prosthesis, measuring a part, where the model of the dental prosthesis is contacted, in the model of the abutment tooth or the model of the alveolar ridge, and thereby producing the three-dimensional shape data of the model of the dental prosthesis on the basis of the each measured values. The model of the dental prosthesis is formed with the wax, synthetic resin or the like. (Hereinafter, this method is referred to as "the latter production method of the three-dimensional shape data".)

Each of the above production methods of the three-dimensional shape data is sufficiently used, when making the three-dimensional shape data of the dental prosthesis by measuring the model of the dental prosthesis such as the inlay, the crown, the bridge or the like, which does not need the comparatively high measuring accuracy and processing accuracy, to thereby make the dental prosthesis by cutting the block for cutting of the dental prosthesis by the automatic cutting machine on the basis of the produced three-dimensional shape data of the dental prosthesis. However, when making the dental prosthesis which need to have a remarkably high measuring and processing accuracies, for example, the dental prosthesis for an implant applied to only one implant fixture, both of the above production methods of the three-dimensional shape data have the problems that it is remarkably difficult to produce the dental prostheses having the necessary dimensional accuracy.

More particularly, the dental prosthesis for the implant applied to only one implant fixture is provided and fixed at an intra-oral side part of the implant fixture embedded into the jawbone, directly or through the abutment. An engaging portion engaged with the intra-oral side part of the implant fixture is projected and/or recessed on the jaw bone side of such the dental prosthesis for the implant, so as to provide the dental prosthesis at a desired rotational position around the axis of the implant fixture, when the dental prosthesis is fixed at the intra-oral side part of the implant fixture.

As for the engaging portion projected and/or recessed on the jaw bone side of the dental prosthesis for the implant, an engaging part is formed to have a sectional shape other than that of a rotary body (hexagonal pillar shape or recessed shape in general). Thus, when the three-dimensional shape data of the model of the dental prosthesis for the implant is produced by the above described former production method of the three-dimensional shape data, there is a problem that the engaging portion cannot be accurately measured, since laser light of the laser sensor of the measuring part can not reach to the inner part of the engaging portion, and the placing table or the XY tables becomes an obstacle, when measuring the part placed on the placing table side of the engaging part. On the other hand, when the three-dimensional shape data of the model of the dental prosthesis for the implant is produced by the above described latter production method of the three-dimensional shape data, the both measured values of the portion on the engaging portion side of the model of the dental prosthesis and the other portion than the engaging portion side thereof are measured by dividing two times respectively. Thus, when the three-dimensional shape data of the model of the dental prosthesis is produced on the basis of these values, there is a problem that the possibility for producing the mismatched three-dimensional shape data is remarkably high, that is, the three-dimensional shape data, where the position of the engaging portion is deviated with respect to the other portion, may be made. Further, there are problems that, when such the deviation is even slightly generated, the dental prosthesis interferes the adjacent tooth at the time of fixing the actually produced dental prosthesis at the implant fixture and that, in the worst case, the produced dental prosthesis cannot be fixed at the implant fixture to become a waste.

Further, the engaging portion of the dental prosthesis for the implant has a polygonal shape having corner parts, for example, regular hexagon in general, so that there is a problem that it is difficult to accurately measure this engaging portion by the laser sensor of the general three-dimensional measuring device. Further, if the produced three-dimensional shape data of the engaging portion of the dental prosthesis is even slightly differed from the actual shape of the engaging portion of the model of the dental prosthesis, there may be problems that the dental prosthesis cannot be engaged well with the implant fixture, or is loosened after fixing with the implant fixture, if the dental prosthesis, which is made by cutting the block for the dental prosthesis by the automatic cutting machine on the basis of the inaccurate three-dimensional data of the dental prosthesis, is fixed with the implant fixture.

Further, even when the former or latter production method can obtain the accurate three-dimensional shape data of the model of the dental prosthesis, there is a problem that the dental prosthesis as the produced three-dimensional shape data cannot be accurately produced when the engaging portion has the shape having the corner parts, since the automatic cutting machine is used for cutting the block using rotationally cutting tool in general, where the automatic cutting machine makes the dental prosthesis on the basis of the three-dimensional shape data of the model of the dental prosthesis.

SUMMARY OF THE INVENTION

The present invention solves the above-mentioned problems of the conventional techniques, and the primary objective of the present invention is to provide the production method of the three-dimensional shape data of the dental prosthesis, where the data is for cutting the block for cutting the dental prosthesis to have the same shape as the measured object using the three-dimensional measuring device by the automatic cutting machine. This three-dimensional measuring device comprises the rotary table, the XY table, and the measuring part for measuring the three-dimensional coordinates of the shape of the measured object. In this device, the rotary table has the axis of the rotating shaft being the Z axis. The XY table has the placing table for providing the measured object mounting tool in a specified direction, is movable in the X axial direction and the Y axial direction, and is arranged on the rotary table, where the placing table is fixed on the upper part of the XY table. The measuring part measures the three-dimensional coordinates of the measured object, which is mounted on the measured object mounting tool on the placing table, by using one laser sensor, which rotationally moves on one plane containing the Z axis at least around the desired point on the Z axis. More particularly, the primary objective of the present invention is to provide the method suitable for producing the three-dimensional shape data of the dental prosthesis where the engaging portion having the engaging part is projected and/or recessed on the jaw bone side and the engaging part has the cross sectional shape other than that of the rotary body.

The earnest work was carried out in order to solve the above-mentioned problems and, as a result of this, the followings were found. When the block for cutting the dental prosthesis is cut by the automatic cutting machine to thereby produce the dental prosthesis, the engaging portion and an the portion other than the engaging portion are not machined simultaneously, but only the portion other than the engaging portion is machined using the block for cutting the dental prosthesis where the engaging portion having the approximately same shape as the engaging portion of the model of the dental prosthesis is preformed. The engaging portion is projected and/or recessed on the jawbone side and has the engaging part having the cross sectional shape other than that of the rotary body. Then, the above-mentioned problems of the measuring accuracy of the three-dimensional measuring device and the processing accuracy of the automatic cutting machine, or the like can be solved.

However, the following problem was found. When the block for cutting the dental prosthesis, where the engaging portion is preformed, is cut by the automatic cutting machine on the basis of the three-dimensional shape data of the model of the dental prosthesis, which is produced by the three-dimensional measuring device, the three-dimensional shape data other than the engaging part of the model of the dental prosthesis must be inputted into the automatic cutting machine, so as to correctly position the positioning relationship between the engaging portion, which is preformed in the block for cutting the dental prosthesis provided in the automatic cutting machine, and the three-dimensional shape data of the portion other than the engaging part of the produced model, with the positioning relationship between the engaging portion and the portion other than the engaging portion of the model of the dental prosthesis. Thus, it is remarkably difficult to correctly input the data while grasping these relationships. Further, when these relationships are deviated even a little, the dental prosthesis, in which the relationship between the portion other than the engaging portion and the preformed engaging portion is deviated, is produced. The portion other than the engaging portion is cut by the automatic cutting machine on the basis of the three-dimensional shape data of the model of the dental prosthesis, and the engaging portion is preformed in the block for cutting the dental prosthesis. Thus, for example, when such the dental prosthesis is fixed at the implant fixture, the aesthetic appreciation is remarkably decreased since the directivities of such the dental prosthesis and the adjacent tooth are deviated. Further, since the dental prosthesis is interfered with the adjacent tooth when such the dental prosthesis is fixed at the implant fixture, the produced dental prosthesis cannot be sufficiently engaged with the implant fixture.

Then, the further earnest work is carried out for producing the dental prosthesis, without deviating the positions of the portion other than the engaging portion and the engaging portion, where the portion other than the engaging portion is cut by the automatic cutting machine on the basis of the three-dimensional shape data of the model of the dental prosthesis, and the engaging portion is preformed in the block for cutting the dental prosthesis. As a result of this, the followings were found out. As for the preformed block for cutting the dental prosthesis, where the engaging portion has the approximately same shape as the engaging portion of the model of the dental prosthesis and is provided in the automatic cutting machine, a reference Z axis positioned in the engaging portion and a reference direction on a plane vertically crossed with the Z axis are pre-specified respectively, where the engaging portion has the cross sectional shape other than that of the rotary body. Thereafter, the three-dimensional shape data of the dental prosthesis, where the three-dimensional coordinates of the shape other than the engaging portion of the model of the dental prosthesis 3 using the Z axis as reference and the reference direction are integrated, is produced. Then, when the block for cutting the dental prosthesis, in which the engaging portion is preformed, is cut by the automatic cutting machine on the basis of such the three-dimensional shape data of the dental prosthesis, the dental prosthesis, where the positing relationship between the portion other than the engaging portion cut by the automatic cutting machine and the engaging portion preformed in the block for cutting the dental prosthesis, and the relationship between the engaging portion and the portion other than the engaging portion in the model of the dental prosthesis correctly meet, can be produced.

Further, the followings are also found out to complete the present invention. For producing such the three-dimensional shape data of the dental prosthesis by using the three-dimensional measuring device, while the Z axis pre-specified in the engaging part of the engaging portion of the model of the dental prosthesis is aligned with the rotary axis of the rotary table having the axis of the rotating shaft being the Z axis, the rotary table is rotated using, as the reference, pre-specified direction of the engaging part of the engaging portion of the model of the dental prosthesis, and the three-dimensional coordinate of the shape other than the engaging portion of the model of the dental prosthesis is measured by the measuring part. Then, it is possible to produce the three-dimensional shape data of the dental prosthesis, where the three-dimensional coordinates of the shape other than the engaging portion of the model of the dental prosthesis using Z axis as the reference is integrated with the pre-specified direction of the mounting part.

That is, the present invention is the production method of the three-dimensional shape data of the dental prosthesis, where the data is for cutting the block for cutting the dental prosthesis to have the same shape as that of the measured object using the three-dimensional measuring device by the automatic cutting machine. This three-dimensional measuring device comprises the rotary table, the XY table, and the measuring part for measuring the three-dimensional coordinates of the shape of the measured object. In this device, the rotary table has the axis of the rotating shaft being the Z axis. The XY table has the placing table for providing the measured object mounting tool while specifying a providing direction, is movable in an X axial direction and a Y axial direction, and is arranged on the rotary table, where the placing table is fixed on the upper part of the XY table. The measuring part measures the three-dimensional coordinates of the shape of the measured object, which is mounted on the measured object mounting tool on the placing table, by using one laser sensor, which rotationally moves on one plane around Z axis at least centering on the desired point on the Z axis.

This method comprises the steps of:

a model preparing step for preparing the model of the dental prosthesis to become the measured object, where the engaging portion is projected and/or recessed on the jawbone side and has the engaging part having a cross sectional shape other than that of the rotary body, a model providing step for preparing the measured object mounting tool, which comprises a cylindrical part, a mounting part on the upper face side of the cylindrical part, and a placing part, and engaging the engaging part of the engaging potion of the model of the dental prosthesis with the mounting part of the measured object mounting tool, where the mounting part has a shape for engaging with the engaging part of the engaging portion of the model of the dental prosthesis and formed so as to position a prolonged line of the center axis of the cylindrical part in the engaging part, and the placing part is formed and put on the placing table so as to have the center axis of the cylindrical part being vertical with respect to the upper surface of the XY table and the pre-specified direction of the mounting part being aligned with the specified providing direction of the placing table, when the lower surface of the cylindrical part is put on the placing table on the XY table, a mounting tool placing step for placing the measured object mounting tool having the model of the dental prosthesis on the placing table, a both axes aligning step for moving the XY table in the X and/or the Y axis directions in order to align the center axis of the cylindrical part of the measured mounting tool with the Z axis, and a model measuring step for rotating the XY table around the Z axis using the specified reference providing direction of the placing table, rotationally moving the laser sensor, and measuring the three-dimensional coordinates of the shape other than the engaging portion of the model of the dental prosthesis and pre-specified direction of the mounting part referencing the Z axis by the measuring part.

By carrying out these steps in order, the three-dimensional shape data of the dental prosthesis for cutting the block for cutting the dental prosthesis by the automatic cutting machine, where the block has the engaging portion having the approximately same shape as the engaging portion of the model of the dental prosthesis beforehand, can be produced.

Further, the followings are also found out. When the cross sectional shape of the mounting part of the measured object mounting tool has the shape where the completely same outside shape appears repeatedly for every 360 degree/n (n is a positive integer of 2 or more), and a figure formed by n time rotations is not circular, the produced dental prosthesis can correspond to the dental prosthesis for the implant applied only one implant fixture having the general engaging portion. Further, since the engaging portion of the produced dental prosthesis has the shape having no part where remarkably strong force is applied around the center axis, the excellent dental prosthesis can be produced, so that is it preferable.

Further, the followings are also found out. When a three-dimensional measuring device comprising an arithmetic process part is used, and the arithmetic process part is for arithmetic processing of the measured value of the three-dimensional coordinates of the shape of the measured object measured by the measuring part, the three-dimensional shape data of the dental prosthesis having various embodiments can be produced, so that it is preferable. Further, in the three-dimensional measuring device having such the arithmetic process part, when the arithmetic process part is for changing the three-dimensional coordinates of the shape other than the engaging portion using Z axis as a reference, to the data for displaying image of a computer, or when the arithmetic processing part is for changing the X and Y axes in the three dimensional coordinates of the shape other than the engaging portion using Z axis as the reference, to the three-dimensional coordinates having new X and Y axes, where a point of the pre-specified direction of the mounting part of the measured object mounting tool being orthogonally crossed with the Z axis is the origin of the new X and Y axes and the pre-specified direction of the mounting part of the measured object mounting tool becomes the pre-specified direction on the coordinates indicated by the new X and Y axes, or when the arithmetic processing part has a compensation function for compensating a line to a smooth continuous line which is drawn on the basis of the three-dimensional coordinates of the shape other than the engaging portion of the model of the dental prosthesis using Z axis as the reference, the three-dimensional shape data of the dental prosthesis can be subjected to the various processing process. Thus, it is preferable.

Further, when the both axes aligning step comprises the steps of:

a mounting tool coordinate measuring step for measuring two-dimensional XY coordinates at plural points in even number by the measuring part $1d$ of the three-dimensional measuring device, where the XY coordinates are positioned on an outer circumference of the cylindrical part $2a$ of the measured object mounting tool, a compensation value calculating step for calculating numerical total values of the X axis coordinate and Y axis coordinate of each point, dividing each total value by the number of the points to thereby obtain the XY coordinates of the center axis of the measured object mounting tool using the Z axis as the origin, calculating the difference in coordinate of the two-dimensional XY coordinates and the origin of the center axis of the measured object mounting tool, and thereby obtaining the compensation value of the center axis of the measured object mounting tool, and a position compensating step for moving the XY table in the X and/or Y axial directions on the basis of the compensation value to thereby align the center axis of the measured object mounting tool with the Z axis, there are the following advantages. When the moving accuracy of the drive means to move the XY table in the X and/or Y axial directions is decreased with the passage of time, and it becomes difficult to easily align the center axis of the cylindrical part of the measured object mounting tool with the Z axis, despite of inputting data into the drive means to move to the position where the center axis of the cylindrical part is aligned with the Z axis, the both axes can be aligned correctly and automatically, so that it is preferable. Further, in such the both axes aligning step, when the mounting tool coordinate measuring step, the compensation value calculating step and the position compensating step are repeated, until the compensation value calculated by the compensation value calculating step becomes less than the minimum unit capable of moving the XY table, the center axis of the cylindrical part of the measured object mounting tool can be aligned with the Z axis more correctly, so that it is preferable.

The production method of the three-dimensional shape data according to the present invention comprises the above-mentioned constitution. Thus, this method is suitable for producing the three-dimensional shape data of the dental prosthesis where the engaging portion having the engaging part in the cross sectional shape other than that of the rotary body is projected and/or recessed. Further, the present invention has the constitution for measuring the measured object mounting tool having the model of the dental prosthesis, where the tool is put on the placing table of the existing three-dimensional measuring device. Thus, the method can be carried out only by preparing the measured object mounting tool corresponding to the model of the dental prosthesis without making big modification or processing of the existing three-dimensional measuring device. As a result of this, the present invention can be applied for measuring not only the measured object of the dental prosthesis, where the engaging portion is projected and/or recessed on the jawbone side and has the engaging part in the cross sectional shape other than that of the rotary body, but also the following various measured objects without introducing a new three-dimensional measuring device, to thereby produce the three-dimensional shape data. The present invention can be applied for measuring the small measured object such as the model of the small type dental prosthesis applied to a small number of teeth such as the inlay, the crown or the like, and the large measured object such as the model of the large type dental prosthesis applied to a large number of teeth such as the bridge or the like, or the gypsum model of a large number of remaining teeth.

Further, the cross sectional shape of the mounting part of the measured object mounting tool comprises the shape, where the completely same outside shape appears repeatedly for every 360 degree/n rotation around the prolonged line of the center axis of the cylindrical part (n is a positive integer of 2 or more), and the figure formed by n time rotations is not circular. Then, when the produced dental prosthesis is the dental prosthesis for the implant, which is applied to only one conventional implant fixture having the general engaging portion, this mounting part can be applicable, so that it is preferable. Further, since the engaging portion of the produced dental prosthesis has the shape which has no parts applied with the remarkably strong force around the center axis, the excellent dental prosthesis can be produced, so that is it preferable.

Further, when the three-dimensional measuring device comprising the arithmetic process part is used, where the arithmetic process part is for arithmetic processing of the measured value of the three-dimensional coordinates of the shape of the measured object measured by the measuring part, the three-dimensional shape data of the dental prosthesis in various embodiments can be produced, so that it is preferable. Further, the three-dimensional shape data of the dental prosthesis can be subjected to various processing, so that it is preferable. Further, in the three-dimensional measuring device comprising such the arithmetic process part, when the arithmetic process part is for changing the three-dimensional coordinate of the shape other than the engaging portion of the model of the dental prosthesis, which uses Z axis as the reference, to the data for displaying the image of the computer, the image of the dental prosthesis to be produced can be easily grasped. Further, for example, when the data for displaying the image of the adjacent tooth or the like of the part applied with the dental prosthesis is also inputted to be displayed with the image of the dental prosthesis, the image of an occulussal surface or a contacting surface with the adjacent tooth of the dental prosthesis can be easily grasped. Thus, on the basis of this data, the produced three-dimensional shape data of the dental prosthesis can be corrected to have the suitable shape, so that it is preferable. Further, when the arithmetic process part is for changing the X and Y axes in the three dimensional coordinates of the shape other than that of the engaging portion using Z axis as the reference to the three-dimensional coordinate having new X and Y axes, where the pre-specified direction of the mounting part of the measured object mounting tool is orthogonally crossed with the Z axis and becomes a specified direction on the coordinates indicated by new X and Y axes having the origin at the cross point, for example, in the case of cutting the block for cutting the dental prosthesis provided in the automatic cutting machine, the data required by the automatic cutting machine in the three-dimensional measuring device is automatically produced, even when the relationship between the pre-specified direction of the three-dimensional shape data required by the automatic cutting machine and the X and Y axes and the relationship between the pre-specified direction of the mounting part of the measured object mounting tool of the three-dimensional coordinates measured by the three-dimensional measuring device and the X and Y axes are not conformed. Thus, the efficiency of the setting work of the automatic cutting machine can be improved. Furthermore, when the arithmetic process part is the part having the compensation function for compensating the line to the smooth continuous line, where the line is drawn on the basis of the three-dimensional coordinates of the shape other than the engaging portion of the model of the dental prosthesis using Z axis as the reference, the shape other than the engaging portion on the three-dimensional shape data becomes smooth. Thus, uncomfortable feeling can be made minimum when the produced dental prosthesis is fixed in the oral cavity, so that it is preferable.

Further, when the both axes aligning step comprises the steps of:

the mounting tool coordinate measuring step for measuring the two-dimensional XY coordinates of plural points in even numbers positioned on an outer circumference of the cylindrical part of the measured object mounting tool by the measuring part of the three-dimensional measuring device, the compensation value calculating step for calculating numerical total value of the X axis coordinate and numerical total value of the Y axis coordinate of each measured point, dividing each total value by the number of the measured points to thereby obtain the XY coordinates of the center axis of the measured object mounting tool using the Z axis as the origin, calculating the difference of the coordinates between the two-dimensional XY coordinates and the origin of the center axis of the measured object mounting tool, and thereby obtaining the compensation value of the center axis of the measured object mounting tool, and the position compensating step for moving the XY table in the X and/or Y axial directions on the basis of the compensation value to thereby align the center axis of the measured object mounting tool with the Z axis, there are the following advantages. When the moving accuracy of the drive means to move the XY table of the three-dimensional measuring device in the X and/or Y axial directions is decreased with the passage of time, and it becomes difficult to easily align the center axis of the cylindrical part of the measured object mounting tool with the Z axis, despite of inputting data into the drive means to move to the position where the center axis of the cylindrical part is aligned with the Z axis, the both axes can be aligned correctly and automatically, so that it is preferable. Further, when the moving accuracy of the drive means moving the XY table in the X and/or Y axial directions in the three-dimensional measuring device is not decreased, the drive means of the XY table moves to the position where the center axis of the cylindrical part of the measured object mounting tool is aligned with the Z axis, to thereby align the both axes automatically. Thus, it is preferable. Further, in such the both axes aligning step, the mounting tool coordinate measuring step, the compensation value calculating step and the position compensating step are repeated until the compensation value calculated by the compensation value calculating step becomes less than the minimum unit capable of moving the XY table. Then, the center axis of the cylindrical part of the measured object mounting tool can be aligned with the Z axis more correctly, so that it is preferable.

DETAILED DESCRIPTION OF PREFERRED EMBODIMENT

Hereinafter, the production method of the three-dimensional shape data of the dental prosthesis according to the present invention is concretely explained with drawings.

Figure 1:
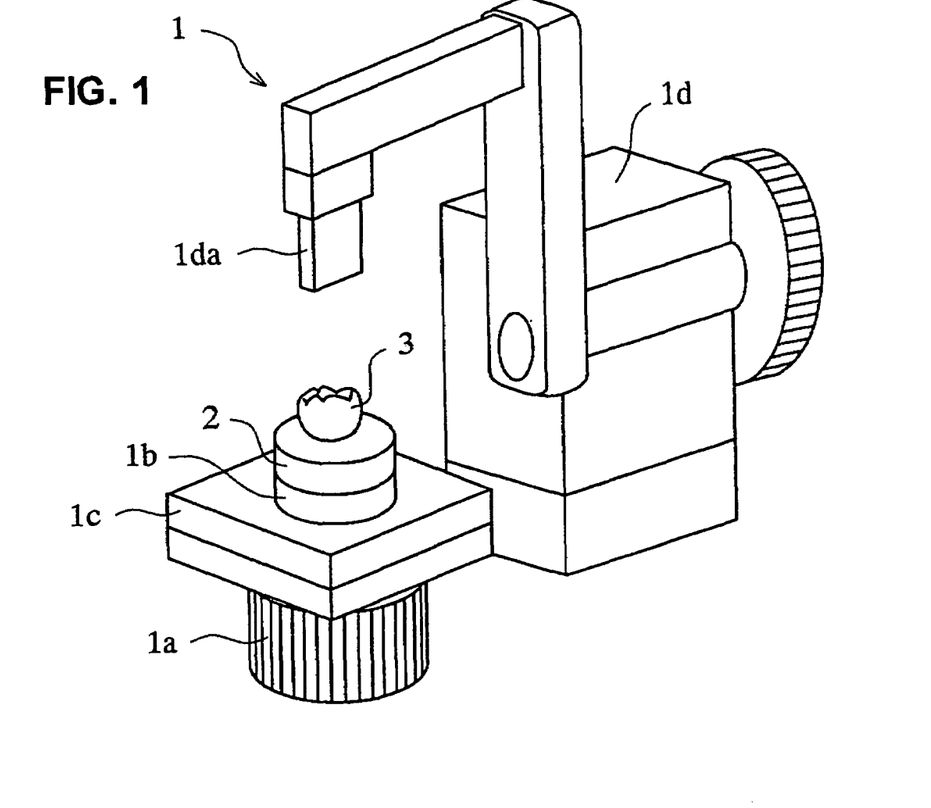
FIG. 1 is a perspective explanation view schematically illustrating one example of a three-dimensional measuring device used in the present invention.
Figure 2:
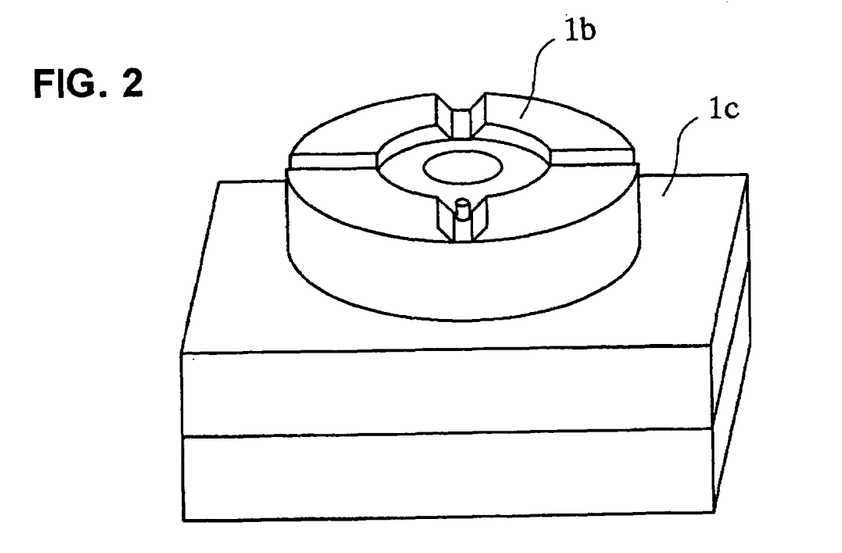
FIG. 2 is a perspective enlarged explanation view illustrating a shape of an upper part of a placing table in the state where a measured object mounting tool is removed from the placing table of the three-dimensional measuring device illustrated in FIG. 1.
Figure 3:
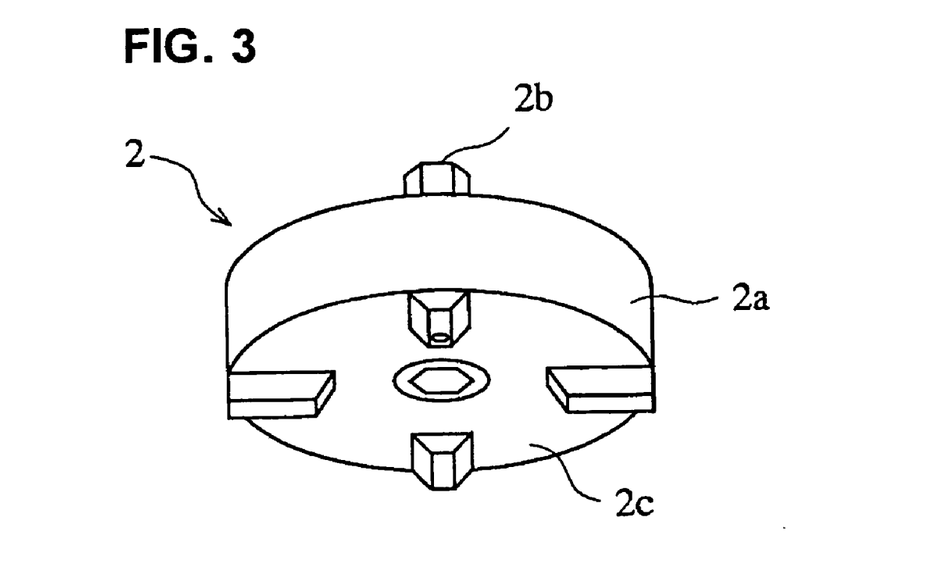
FIG. 3 is a perspective enlarged explanation view illustrating a lower part of the measured object mounting tool removed from the placing table of the three-dimensional measuring device illustrated in FIG. 1.
Figure 4:
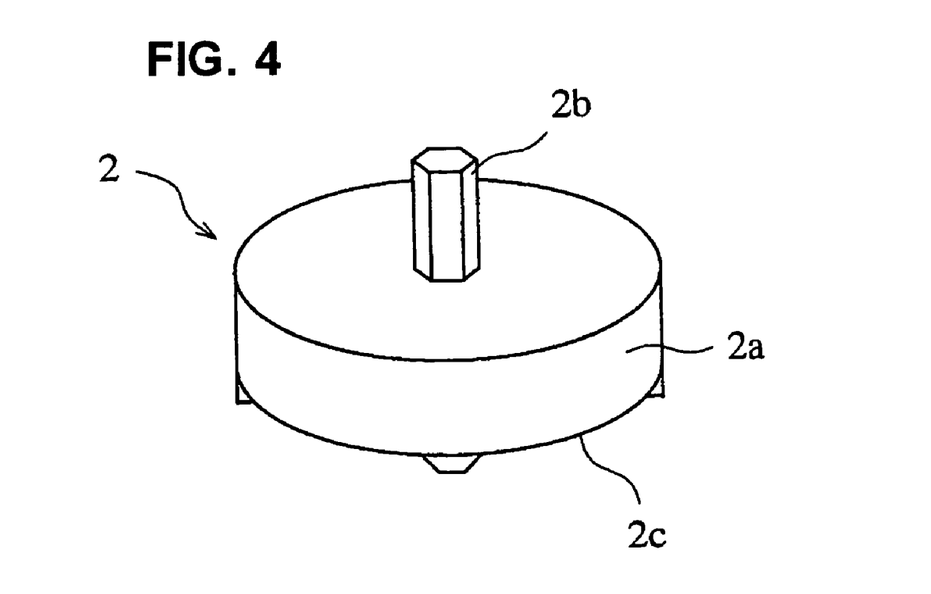
FIG. 4 is a perspective enlarged explanation view illustrating an upper part of the measured object mounting tool removed from the placing table of the three-dimensional measuring device illustrated in FIG. 1.
Figure 5:
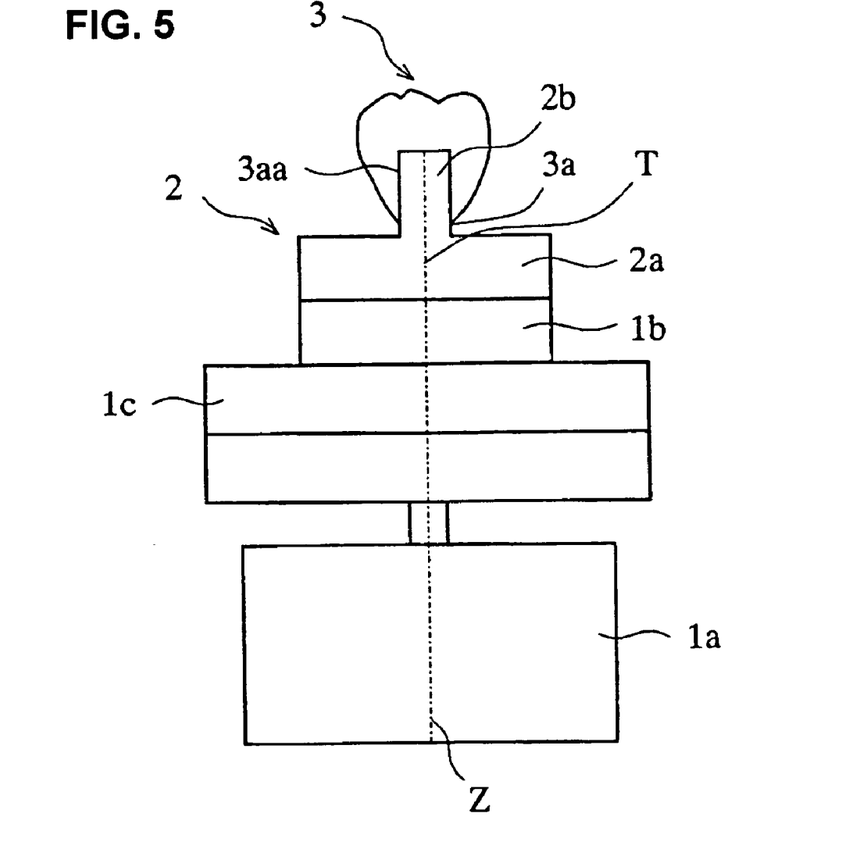
FIG. 5 is a sectional explanation view schematically illustrating the state where the center axis of the cylindrical part is aligned with the Z axis of the measured object mounting tool.
Figure 6:
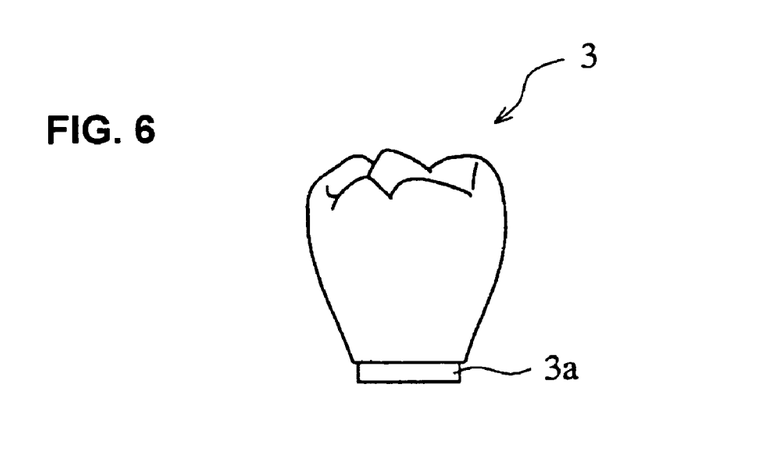
FIG. 6 is a front explanation view illustrating one example of the model of the dental prosthesis used in the present invention.
Figure 7:
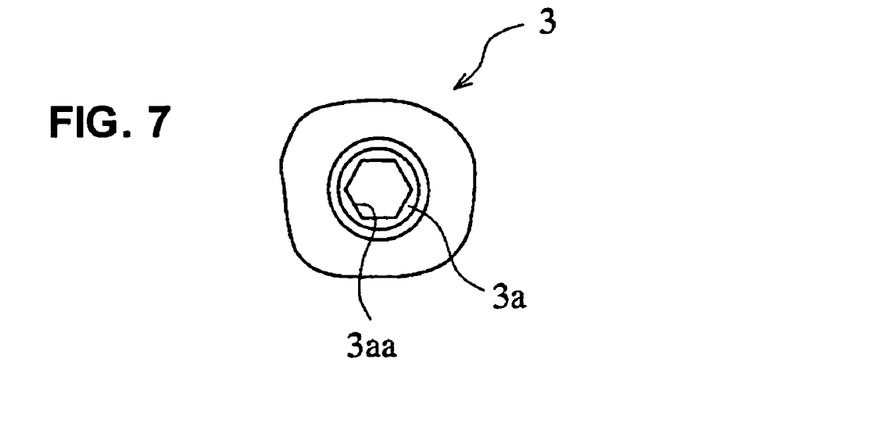
FIG. 7 is an explanation view of a bottom face of FIG. 6.
Figure 8:
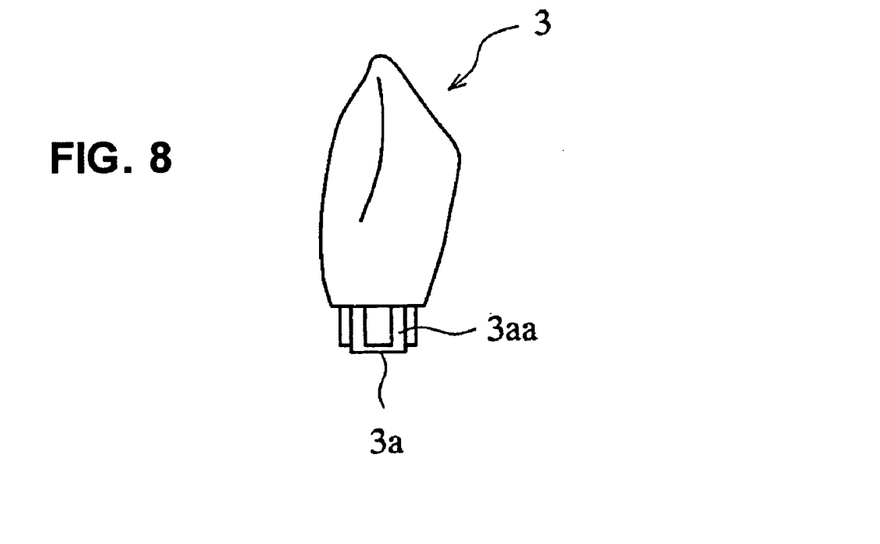
FIG. 8 is a front explanation view illustrating another example of the model of the dental prosthesis used in the present invention.
Figure 9:
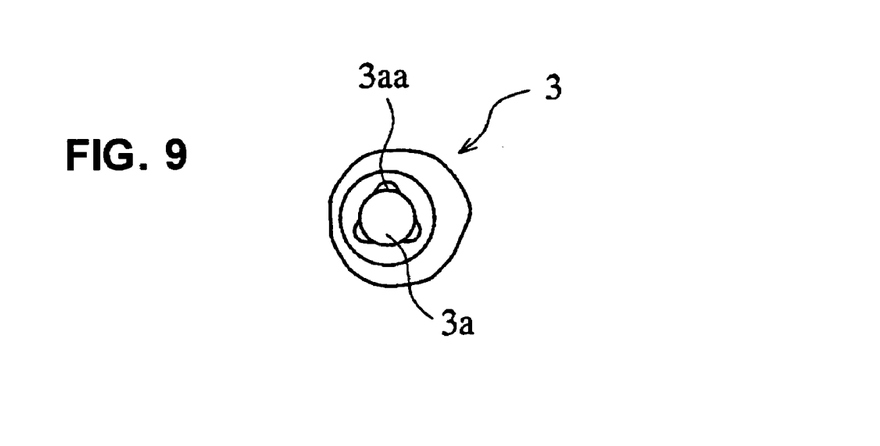
FIG. 9 is an explanation view of a bottom face of FIG. 8.
Figure 10:
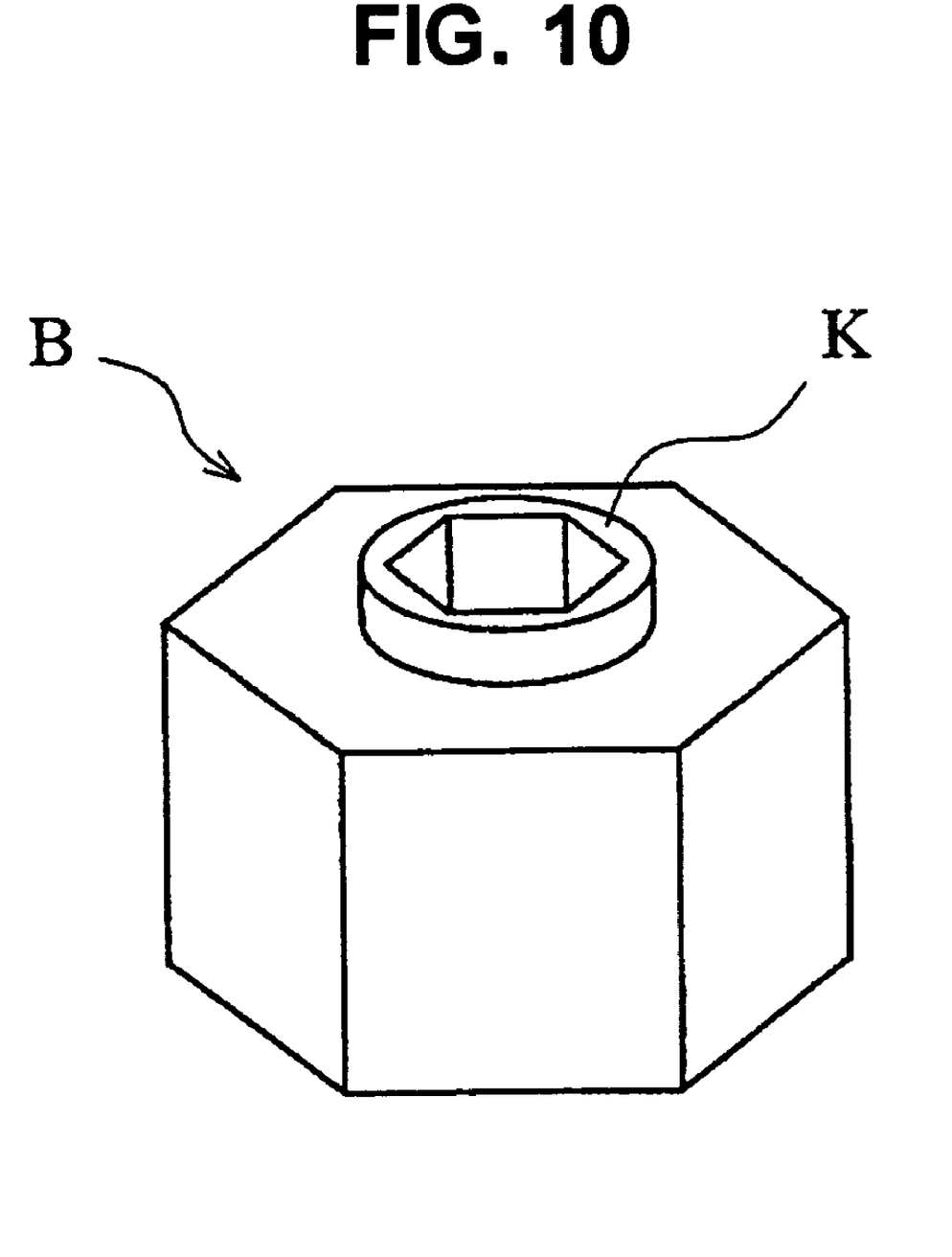
FIG. 10 is a perspective explanation view illustrating one example of a block for cutting the dental prosthesis to be cut on the basis of a three-dimensional shape data of the dental prosthesis produced by the present invention.

FIG. 1 is a perspective explanation view schematically illustrating one example of a three-dimensional measuring device used in the present invention. FIG. 2 is a perspective enlarged explanation view illustrating a shape of an upper part of a placing table in the state where a measured object mounting tool is removed from the placing table of the three-dimensional measuring device illustrated in FIG. 1. FIG. 3 is a perspective enlarged explanation view illustrating a lower part of the measured object mounting tool removed from the placing table of the three-dimensional measuring device illustrated in FIG. 1. FIG. 4 is a perspective enlarged explanation view illustrating an upper part of the measured object mounting tool removed from the placing table of the three-dimensional measuring device illustrated in FIG. 1. FIG. 5 is a sectional explanation view schematically illustrating the state where the center axis of the cylindrical part is aligned with the Z axis of the measured object mounting tool. FIG. 6 is a front explanation view illustrating one example of the model of the dental prosthesis used in the present invention. FIG. 7 is an explanation view of a bottom face of FIG. 6. FIG. 8 is a front explanation view illustrating another example of the model of the dental prosthesis used in the present invention. FIG. 9 is an explanation view of a bottom face of FIG. 8. FIG. 10 is a perspective explanation view illustrating one example of a block for cutting the dental prosthesis to be cut on the basis of a three-dimensional shape data of the dental prosthesis produced by the present invention.

In the drawings, 1 is a three-dimensional measuring device used in the method of the present invention. As illustrated in FIG. 1, the three-dimensional measuring device 1 comprises a rotary table 1a, a XY table 1c, and a measuring part 1d. In this device, the rotary table 1a has an axis of a rotating shaft, which is a Z axis. The XY table 1c has a placing table 1b for providing a measured object mounting tool 2, which is fixed on the upper part thereof, is movable in the X axial direction and the Y axial direction and is arranged on the rotary table 1a. The measuring part 1d is for measuring the three-dimensional coordinates of the shape of the measured object by one laser sensor 1da, where the measured object is mounted on the measured object mounting tool 2 on the placing table 1b. The laser sensor 1da can rotationally move on one plane containing the Z axis at least around a desired point on the Z axis. More preferably, when the one laser sensor 1da can move in the Z axial direction, the height when starting the rotationally moving can be adjusted.

The three-dimensional measuring device 1 is used for measuring the three-dimensional coordinates of the shape of the measured object mounted on the measured object mounting tool 2 by the measuring part 1d, where this tool is provided at the upper part of the placing table 1b and the providing direction of this tool is specified, to thereby produce the three-dimensional shape data of the dental prosthesis for cutting a block B for cutting the dental prosthesis by the automatic cutting device, in order to have the same shape as that of the measured object.

For measuring the three-dimensional coordinates of the shape of the measured object using the three-dimensional measuring device 1, the following steps are carried out. The coordinates are measured by the steps of rotating the object around the Z axis by the rotary table 1a, where the Z axis is the center axis of the rotary shaft of the rotary table 1a, moving the measured object to the X axis direction and Y axis direction by the XY table 1c, where the object is mounted on the measured object mounting tool 2 provided at the upper part of the placing table, rotationally moving the one laser sensor 1da itself of the measuring part 1d on one plane containing the Z axis around the desired point on the Z axis, irradiating the laser light on the surface of the measured object by the one laser sensor 1da, receiving the laser light reflected from the face of the measured object, measuring the three-dimensional coordinates of each point of the surface of the measured object on the basis of a position of the laser sensor 1*da*, a light receiving angle of the laser light, a light receiving amount of the laser light, time from irradiating to receiving the light, or the like, when receiving the laser light by the measuring part 1*d*, and thereby, obtaining the three-dimensional coordinates of the shape of the measured object on the basis of a plurality of these measuring points.

The placing table 1*b* fixed at the XY table 1*c* of the three-dimensional measuring device 1 is formed to have the shape capable of specifying the providing direction and providing the measured object mounting tool 2 on the upper part thereof. For example, as illustrated in FIG. 3, the measured object mounting tool 2 is radiately provided four engaging protrusions at the lower part and has one engaging bored hole for deciding the position at one of the engaging portrusions. As illustrated in FIG. 2, the placing table 1*b* is formed to radiately provide four engaging grooves at the upper part so as to engage with the four engaging protrusions of the measured object mounting tool 2 and has a pin for deciding the position, which is fitted into the hole for deciding the position.

Further, as for the three-dimensional measuring device 1, when the three-dimensional measuring device provided with the arithmetic process part, which is for arithmetic processing the measured value of the three-dimensional coordinates of the shape of the measured object measured by the measuring part is used, not only the three-dimensional shape data of the dental prosthesis having the various shapes can be produced but also various modification processing can be applied to the three-dimensional shape data of the dental prosthesis, so that it is preferable.

Further, when the arithmetic process part is the part where the three-dimensional coordinates of the shape other than the engaging portion 3*a* of the model 3 of the dental prosthesis using Z axis as the reference is changed to the data for displaying the image of the computer, the dental technician can easily grasp the image of the dental prosthesis to be produced. Further, for example, when the data for displaying the image of the adjacent tooth or the like of the part applied with the dental prosthesis is also inputted to be displayed with the image of the dental prosthesis, the image of the occulussal surface of the dental prosthesis or the contacting surface with the adjacent tooth can be easily grasped. Thus, on the basis of this image, the produced three-dimensional shape data of the dental prosthesis can be corrected to have the suitable shape, so that it is preferable. Further, when an arithmetic processing part is the part for changing the X and Y axes in the three dimensional coordinates of the shape other than the engaging portion 3*a* of the model 3 of the dental prosthesis using Z axis as the reference to the three-dimensional coordinates having new X and Y axes, where the pre-specified direction of the mounting part 2*b* of the measured object mounting tool 2 being orthogonally crossed with the Z axis and the pre-specified direction of the mounting part 2*b* of the measured object mounting tool 2 becomes a specified direction on the coordinates indicated by new X and Y axes having the origin at the above cross point, it is preferable as, for example, in the case of cutting the block B for cutting the dental prosthesis provided in the automatic cutting machine, the data required by the automatic cutting machine in the three-dimensional measuring device 1 is automatically produced, even when the relationship between the pre-specified direction of the three-dimensional shape data required by the automatic cutting machine and the XY axes, and the relationship between the pre-specified direction of the mounting part 2*b* of the measured object mounting tool 2 of the three-dimensional coordinates measured in the three-dimensional measuring device 1 and the X and Y axes are not aligned. Thus, the efficiency of the setting work of the automatic cutting machine can be improved. Furthermore, when the arithmetic process part is the part having the compensation function for compensating the line to the smooth continuous line, where the line is drawn on the basis of the three-dimensional coordinates of the shape other than the engaging portion 3*a* of the model 3 of the dental prosthesis using Z axis as the reference, the shape other than the engaging portion on the three-dimensional shape data of the dental prosthesis becomes smooth. Thus, uncomfortable feeling can be made minimum when the produced dental prosthesis is fixed in the oral cavity, so that it is preferable.

As the arithmetic process part of the three-dimensional measuring device 1, for example, a part comprising an arithmetic process device and a display, which are additionally built in the three-dimensional measuring device 1, may be used. However, if this part is a computer separately connected with the three-dimensional measuring device 1, this part can cooperate with various software introduced into the computer, the connected various peripheral devices or the like, so that it is preferable.

2 is a measured object mounting tool, which can be put on the upper part of the placing table 1*b* on the XY table 1*c* of the three-dimensional measuring device 1 with specifying the providing direction. The measured object mounting tool 2 comprises a cylindrical part 2*a*, a mounting part 2*b* on the upper surface side of the cylindrical part 2*a* and a placing part 2*c*. The mounting part 2*b* has a shape for engaging with the engaging part 3*aa* of the engaging portion 3*a* of the model 3 of the dental prosthesis, and formed so as to position a prolonged line of the center axis T of the cylindrical part 2*a* in the engaging part 3*aa*. The placing part 2*c* is formed and put on the placing table 1*b* so as to make the center axis T of the cylindrical part 2*a* to be vertical with respect to the upper surface of the XY table 1*c* and to align the pre-specified direction of the mounting part 2*b* with the specified providing direction of the placing table 1*b*, when the lower surface of the cylindrical part 2*a* is put on the placing table 1*b* on the XY table 1*c*.

The mounting part 2*b* is provided on the upper face side of the cylindrical part 2*a* of the measured object mounting tool 2, where the mounting part 2*b* has the shape for engaging with the engaging part 3*aa* of the engaging portion 3*a*, and is formed so as to position the prolonged line of the center axis T of the cylindrical part 2*a* in the engaging part 3*aa*. Further, for example, when the engaging part 3*aa* of the engaging portion 3*a*, which is mounted to the mounting part 2*b*, is recessed on the jawbone side as illustrated in FIGS. 6 and 7, the mounting part 2*b* is projected so as to have the pillar shape as illustrated in FIG. 4. Further, for example, when the engaging part 3*aa* of the engaging portion 3*a* is projected on the jawbone side as illustrated in FIGS. 8 and 9, the mounting part 2*b* is recessed so as to have the hole shape (not illustrated in the figures).

Further, as the cross sectional shape of the mounting part 2*b* of the measured object mounting tool 2, it is not limited if this shape is a shape capable of engaging with the engaging part 3*aa*, which has the shape other than that of the rotary body, in the engaging portion 3*a* of the model 3 of the dental prosthesis, that is, the shape other than a perfect circle. However, the preferable cross sectional shape of the mounting part 2*b* of the measured object mounting tool 2 is a shape where the completely same outside shape appears repeatedly for every 360 degree/n rotation around the prolonged line of the center axis T of the cylindrical part 2a (n is a positive integer of 2 or more), and the figure formed by n time rotations is not circular. Such conditions are satisfied by a shape being right polygon like the engaging part 3aa illustrated in FIGS. 6 and 7 or a shape being a rotationally symmetric shape like the engaging part 3aa illustrated in FIGS. 8 and 9, where circular arcs are projected at equal intervals around the right circle. When the cross sectional shape of the mounting part 2b of the measured object mounting tool 2 has the above shapes, the mounting part 2b can be employed when the produced dental prosthesis is the dental prosthesis for the implant, which is applied to only one implant fixture having the conventional engaging portion, so that it is preferable. Further, since the engaging portion of the produced dental prosthesis has the shape having no part where remarkably strong force is applied around the center axis, the excellent dental prosthesis can be produced, so that is it preferable.

The placing part 2c is provided on the lower face side of the cylindrical part 2a of the measured object mounting tool 2, where the placing part 2c is formed so as to vertically cross the center axis T of the cylindrical part 2a with respect to the upper surface of the XY table 1c, and to align the pre-specified direction of the mounting part 2b and the pre-specified providing direction of the placing table 1b, when the lower surface of the cylindrical part 2a is put on the placing table 1b on the XY table 1c. As for the placing part 2c of the measured object mounting part 2, for example, when it has the shape that the placing table 1b of the three-dimensional measuring device 1 has the radiately 4 engaging grooves at the upper part thereof and the pin for deciding the position is erected on the one engaging groove, as illustrated in FIG. 2, then, in order to put the placing part 2c on the placing table 1b in the pre-specified direction, the placing part 2c is formed to have the shape that the 4 engaging protrusions is radiately provided and the hole for deciding the position is bored at the one engaging protrusion, as illustrated in FIG. 3.

3 is a model of the dental prosthesis which is the measured object, where the engaging portion 3a having the engaging part 3aa, which has the cross sectional shape other than the shape of the rotary body, is projected and/or recessed on the jawbone side. The model 3 of the dental prosthesis is formed with the material such as the wax, the synthetic resin, gypsum or the like, by a dental technician.

As the model 3 of the dental prosthesis, it is not limited if the engaging portion 3a having the engaging part 3aa is projected and/or recessed on the jaw bone side, where the engaging part 3aa has at least having the cross sectional shape other than that of the rotary body, that is, the cross sectional shape other than the right circle. However, for example, if the model 3 of the dental prosthesis is formed to have the right hexagonal hole shape recessed on the jawbone side, as illustrated in FIGS. 6 and 7, or formed with the cylindrical shape projected on the jawbone side and a plurality of semicircular projection parts provided on the circumference face of the cylindrical shape at equal intervals, as illustrated in FIGS. 8 and 9, then a plurality of ways for mounting direction exists when the model 3 of the dental prosthesis is mounted at the measured object mounting tool 2. Thus, the mounting work becomes easy, so that it is preferable. Further, since the engaging portion of the dental prosthesis to be produced can have the shape having no parts where the remarkably strong force is applied around the center axis, the excellent dental prosthesis can be produced, so that it is preferable.

Next, each step of the production method of the three-dimensional shape data of the dental prosthesis by using the three-dimensional measuring device 1 in the method of the present invention having such the constitution is described in order, where the data is for cutting the block B for cutting the dental prosthesis by the automatic cutting machine to have the same shape as that of the model 3 of the dental prosthesis, which is the measured object.

First, the model preparing steps is carried out for preparing the model 3 of the dental prosthesis, where the engaging portion 3a is projected and/or recessed on the jawbone side and has the engaging part 3aa in the cross sectional shape other than that of the rotary body. Before measuring, the model preparing step is carried out by preparing the model 3 of the dental prosthesis preformed using the material such as the wax, the synthetic resin, the gypsum or the like, by the dental technician or the like.

Then, the model providing step is carried out for preparing the measured object mounting tool 2 and engaging the engaging part 3aa of the engaging potion 3a with the mounting part 2b of the measured object mounting tool 2. The measured object mounting tool 2 comprises the cylindrical part 2a, the mounting part 2b on the upper face side of the cylindrical part 2a, and the placing part 2c. In the measured object mounting tool 2, the mounting part 2b has the shape for engaging with the engaging part 3aa of the engaging portion 3a and is formed so as to position the prolonged line of the center axis T of the cylindrical part 2a in the engaging part 3aa. The placing part 2c is formed so as to be put on the placing table 1b, where the center axis T of the cylindrical part 2a is vertical with respect to the upper face of the XY table 1c and the pre-specified direction of the mounting part 2b is aligned with the specified providing direction of the placing table 1b, when the lower surface of the cylindrical part 2a is put on the placing table 1b on the XY table 1c. The engaging part 3aa is prepared in the model preparing step.

Then, the mounting tool placing step is carried out for placing the measured object mounting tool 2 having the model 3 of the dental prosthesis on the placing table 1b.

At this time, the measured object mounting tool 2 having the model 3 of the dental prosthesis is put on the placing table 1b, where, when the lower surface of the cylindrical part 2a is put on the placing table 1b on the XY table 1c, the center axis T of the cylindrical part 2a is vertical with respect to the upper face of the XY table 1c, and the pre-specified direction of the mounting part 2b is aligned with the specified providing direction of the placing table 1b. Thus, in the model measuring step described below, the pre-specified direction of the mounting part 2b is measured by rotating the XY table 1c around the Z axis on the basis of the specified providing direction of the placing table 1b, to thereby produce the three-dimensional shape data of the dental prosthesis, where the three-dimensional coordinates of the shape other than the engaging portion 3a of the model 3 of the dental prosthesis using the Z axis as a reference axis is integrated with the pre-specified direction of the mounting part 2b.

Then, the both axes aligning step is carried out for moving the XY table 1c in the X and/or the Y axis directions in order to align the center axis T of the cylindrical part 2a of the measured mounting tool 2 with the Z axis.

By the both axes aligning step, as illustrated in FIG. 5, the prolonged line of the center axis T of the cylindrical part 2a of the measured object mounting tool 2 becomes in the state of aligning with the Z axis which is the axis of the rotation shaft of the rotary table 1a, where the prolonged line is positioned in the engaging part 3aa of the engaging portion 3a of the model 3 of the dental prosthesis. Thus, in the model measuring step described below, when the XY table 1c is rotated around the Z axis on the basis of the specified providing direction of the placing table 1b, the model 3 of the dental prosthesis provided at the measured object mounting tool 2 is rotated around the Z axis in the engaging part 3aa of the engaging portion 3a. Thus, it is possible to produce the three-dimensional shape data of the dental prosthesis having the Z axis in the engaging part 3aa of the engaging portion 3a.

For carrying out the both axes aligning step, for example, data is inputted into the drive means moving the XY table 1c in the X and/or Y axial directions so as to move to the position where the center axis T of the cylindrical part 2a is aligned with the Z axis. However, it is preferable that the both axes aligning step comprises the mounting tool coordinate measuring step, the compensation value calculating step and the position compensating step. The mounting tool coordinate measuring step is for measuring the two-dimensional XY coordinates of plural points in even numbers by the measuring part 1d of the three-dimensional measuring device 1, where the XY coordinate is positioned on the outer circumference of the cylindrical part 2a of the measured object mounting tool 2. The compensation value calculating step is for calculating numerical total values of the X axis coordinate and Y axis coordinate of each point, dividing each total value by the number of the points to thereby obtain the XY coordinates of the center axis T of the measured object mounting tool 2 using the Z axis as the origin, calculating the difference in coordinate between the two-dimensional XY coordinates and the origin of the center axis T of the measured object mounting tool 2, and thereby obtaining the compensation value of the center axis T of the measured object mounting tool 2. The position compensating step is for moving the XY table 1c in the X and/or Y axial directions on the basis of the compensation value, to thereby align the center axis T of the measured object mounting tool 2 with the Z axis. When the both axes aligning step comprises these steps, there are the following advantages. When the moving accuracy of the drive means is decreased with the passage of time, where the drive means moves the XY table 1c in the X and/or Y axial directions and it becomes difficult to easily align the center axis T of the cylindrical part 2a of the measured object mounting tool 2 with the Z axis, despite of inputting the data into the drive means to move to the position where the center axis T of the cylindrical part 2a is aligned with the Z axis, the both axes can be aligned correctly and automatically, so that it is preferable. Further, even in the three-dimensional measuring device 1, where the moving accuracy of the drive means is not decreased, the both axes can be automatically aligned without separately inputting the data to move to the position where the center axis T of the cylindrical part 2a of the measured object mounting tool 2 is aligned with the Z axis, so that it is preferable.

Further, in such the both axes aligning step, when the mounting tool coordinate measuring step, the compensation value calculating step and the position compensating step are repeated until the compensation value calculated by the compensation value calculating step becomes less than the minimum unit capable of moving the XY table 1c, the center axis T of the cylindrical part 2a of the measured object mounting tool 2 can be aligned with the Z axis more correctly, so that it is preferable.

Finally, the model measuring step is carried out by rotating the XY table 1c around the Z axis on the basis of the specified providing direction of the placing table 1b, where the model measuring step is for measuring the three-dimensional coordinates of the shape other than the engaging portion 3a using the Z axis as a reference axis and the pre-specified direction of the mounting part 2b are measured by the measuring part 1d, in the state that the measured object mounting tool 2 having the model 3 of the dental prosthesis is placed on the placing table 1b by the mounting tool placing step, the lower surface of the cylindrical part 2a is put on the placing table 1b on the XY table 1c, the center axis T of the cylindrical part 2a is vertical with respect to the upper surface of the XY table 1c, and the pre-specified direction of the mounting part 2b is aligned with the specified providing direction of the placing table 1b, and that the prolonged line of the center axis T of the cylindrical part 2a of the measured object mounting tool 2 is aligned with the Z axis which is the axis of the rotating shaft of the rotary table 1a by the both axes aligning step, where the prolonged line is positioned in the engaging part 3aa of the engaging portion 3a. Then, it is possible to produce the three-dimensional shape data of the dental prosthesis for cutting the block B, where an engaging portion K in approximately same shape as that of the engaging portion 3a of the model 3 of the dental prosthesis is preformed, for cutting the dental prosthesis by the automatic cutting machine.

At this time, as for the three-dimensional shape data of the dental prosthesis produced by the method of the present invention, more particularly, it is the three-dimensional shape data of the dental prosthesis, where the three-dimensional coordinates of the shape other than the engaging portion 3a of the model 3 of the dental prosthesis using the Z axis as a reference axis is integral with the pre-specified direction of the mounting part 2b. On the basis of such the three-dimensional shape data of the dental prosthesis, the block B for cutting the dental prosthesis, where the an engaging portion K is preformed and has an approximately same shape as the that of engaging portion 3a of the model 3 of the dental prosthesis, is cut by the automatic cutting machine. Thus, it is possible to produce the dental prosthesis, where the position relationship between the portion other than the engaging portion K cut by the automatic cutting machine and the engaging portion K preformed in the block B for cutting the dental prosthesis is correctly conformed with the position relationship between the engaging portion 3a and the portion other than the engaging portion 3a in the model 3 of the dental prosthesis.

Next, the method for cutting the block B for cutting the dental prosthesis, where the engaging portion K is preformed and has the approximately same shape as the engaging portion 3a of the dental prosthesis 3, by the automatic cutting machine using the three-dimensional shape data of the dental prosthesis produced by the method of the present invention, is described.

First, the block B for cutting the dental prosthesis, where the engaging portion K has the approximately same shape as the engaging portion 3a is prepared beforehand.

As the block B, for example, the shape in which engaging portion K is preformed as illustrated in FIG. 10 is preferably used and titanium alloies, ceramics before or after sintering, composite resins or the like is used as the materials.

Then, the providing direction when providing the block B in the automatic cutting machine is preset, and the preset providing direction is pre-memorized in the control means for controlling a cutting jig or the like in the automatic cutting machine.

In particular, in the block B for cutting the dental prosthesis, the reference Z axis positioned in the engaging part and the reference direction on the plane vertically crossing with the Z axis are pre-specified respectively in the engaging portion K, which has the cross sectional shape other than that of the rotary body. When the block B is cut by the automatic cutting machine, it is cut in the state where the Z axis and the pre-specified direction in the block B provided in the automatic cutting machine are aligned with the Z axis and the pre-specified direction in the three-dimensional shape data of the dental prosthesis inputted into the control means of the automatic cutting machine. Thus, it is possible to produce the dental prosthesis, where the position relationship between the portion other than the engaging portion K cut by the automatic cutting machine and the engaging portion K preformed in the block B is correctly conformed with the position relationship between the engaging portion 3a and the portion other than the engaging portion 3a in the model 3 of the dental prosthesis.

More particularly, this operation is carried out as follows. First, the providing directions is preset, to decide in which directions the Z axis and the pre-specified direction in the block B are provided to the portion provided with the block B in the automatic cutting machine. Then, the preset providing directions of the Z axis and the pre-specified direction in the block B to the portion provided with the block B, that is, the providing direction of the block B, is pre-memorized in the control means for controlling the cutting jig or the like of the automatic cutting machine.

At this time, an engaging part having the approximately same shape as that of the mounting part 2b of the measured object mounting tool 2 is provided at the portion where the block B is provided in the automatic cutting machine, and the engaging portion K engaged with the engaging part is provided at the block B. Further, those engaging parts are formed so as to direct the block B to the providing direction which is preset when the block B is provided in the automatic cutting machine. Then, the block B can be easily provided in the preset providing direction in the automatic cutting machine, so that it is preferable.

Further, at this time, when the three-dimensional measuring device comprising the arithmetic process part is used as the three-dimensional measuring device 1, where the arithmetic process part is for arithmetic processing of the measured value of the three-dimensional coordinates of the shape of the measured object measured by the measuring part, and, X and Y axes in the three-dimensional coordinates of the shape other than the engaging portion 3a is changed by the arithmetic process part to the three-dimensional coordinates having new X and Y axes, where the pre-specified direction of the mounting part 2b of the measured object mounting tool 2 is orthogonally crossed with the Z axis becomes a pre-specified direction on the coordinate indicated in new X and Y axes, having the origin at the cross point, for example, in the case of cutting the block B for cutting the dental prosthesis provided in the automatic cutting machine, the data required by the automatic cutting machine is automatically produced in the three-dimensional measuring device 1, even when the relationship between the pre-specified direction of the three-dimensional shape data required by the automatic cutting machine and the X and Y axes and the relationship between the pre-specified direction of the mounting part 2b of the measured object mounting tool 2 of the three-dimensional coordinates measured by the three-dimensional measuring device 1 and the X and Y axes are not conformed. Thus, the efficiency of the setting work of the automatic cutting machine can be improved.

After finishing such the preparation, the operation for providing the block B in the automatic cutting machine is carried out at first. At this time, the block B is provided in the automatic cutting machine so as to direct in the predetermined direction.

Next, the three-dimensional shape data of the dental prosthesis, which is produced by the method of the present invention, is inputted to the automatic cutting machine, and the operation for cutting the block B is carried out on the basis of the inputted three-dimensional shape data of the dental prosthesis, where the block B is provided in the automatic cutting machine so as to direct in the preset providing direction.

At this time, the providing direction of the block B for cutting the dental prosthesis, that is, the Z axis and the pre-specified direction in the block B are pre-memorized in the control means for controlling the cutting jig or the like of the automatic cutting machine. Thus, only by inputting the three-dimensional shape data of the dental prosthesis, where the three-dimensional coordinates of the shape other than the engaging portion 3a of the model 3 of the dental prosthesis using the Z axis as a reference axis is integrated with the pre-specified direction of the mounting part 2b, into the automatic cutting machine, the cutting is carried out in the state where the Z axis and the pre-specified direction in the block B provided in the automatic cutting machine are aligned with the Z axis and the pre-specified direction in the three-dimensional shape data of the dental prosthesis, which is inputted into the control means of the automatic cutting machine. Thus, it is possible to produce the dental prosthesis, where the position relationship between the portion other than the engaging portion K cut by the automatic cutting machine and the engaging portion K preformed in the block B is correctly conformed with the position relationship between the engaging portion 3a and the portion other than the engaging portion 3a in the model 3 of the dental prosthesis.

What is claimed is:

1. A method of producing a three-dimensional shape data of a model of a dental prosthesis, wherein said data is subsequently used for cutting a block by an automatic cutting machine to create a dental prosthesis that has the same shape as that of the model of the dental prosthesis, wherein said method comprises the steps of:

providing a model of a dental prosthesis, said model having an engaging portion on the jawbone side, said engaging portion including an engaging part having a first cross sectional shape;

providing a three-dimensional measuring device, said three-dimensional measuring device comprising:

a rotary table rotatable about a Z axis, a XY table, said XY table being movable in both X axial and Y axial directions and arranged on the rotary table, a placing table arranged on the XY table, a mounting tool fixed on an upper part of the placing table specifying a providing direction, said mounting tool comprising a cylindrical part, a mounting part on an upper face side of the cylindrical part, said mounting part having a second cross sectional shape for engaging with the engaging part of the model of the dental prosthesis, said mounting part being formed so as to position a prolonged line of a center axis T of the cylindrical part in the engaging part, and the placing part is formed and placed on said placing table so as to have the center axis T of the cylindrical part being vertical with respect to an upper surface of the XY table, the placing part is formed and placed on said placing table so as to have the center axis T of the cylindrical part being vertical with respect to the upper surface of the XY table, and the mounting part being aligned with the specified providing direction when the lower surface of the cylindrical part is placed on the placing table, and a measuring part for measuring the three-dimensional coordinates of the shape of a model mounted on the mounting tool, said measuring part including a laser sensor rotationally moving on one plane containing the Z axis at least around a desired point on the Z axis;

mounting the engaging part of said model of the dental prosthesis on the mounting part of said mounting tool;

mounting the mounting tool with the model of the dental prosthesis on the placing table;

moving the XY table in the X and/or the Y axis directions in order to align the center axis T of the cylindrical part of the mounting tool with the Z axis; and measuring said model of the dental prosthesis by rotating the XY table via the rotary table around the Z axis using the specified reference providing direction of the placing table and rotationally moving the laser sensor, to thereby produce three-dimensional data of the shape of the model of the dental prosthesis other than the engaging portion of the model.

2. The method of producing the three-dimensional shape data of the dental prosthesis as recited in claim 1, wherein the second cross sectional shape of the mounting part of the mounting tool has the shape where the completely same outside shape appears repeatedly for every 360 degree/n (n is a positive integer of 2 or more) around the prolonged line of the center axis T of the cylindrical part, and a figure formed by n time rotations is not circular.

3. The method of producing the three-dimensional shape data of the dental prosthesis as recited in claim 1, wherein said three-dimensional measuring device further includes an arithmetic process part, said arithmetic process part being used for arithmetic-processing of a measured value of the three-dimensional coordinates of the shape of the model measured by the measuring part of the three-dimensional measuring device.

4. The method of producing the three-dimensional shape data of the dental prosthesis as recited in claim 3, wherein the arithmetic process part changes the three-dimensional coordinates of the shape of the model other than the engaging portion of the model using the Z axis as a reference to data for displaying an image on a computer.

5. The method of producing the three-dimensional shape data of the dental prosthesis as recited in claim 3, wherein the arithmetic process part changes the X and Y axes in the three dimensional coordinate of the shape of the model other than the engaging portion of the model using Z axis as the reference, to the three-dimensional coordinates having new X and Y axes, where a point of the pre-specified direction of the mounting part of the mounting tool being orthogonally crossed with the Z axis is the origin of the new X and Y axes and the pre-specified direction of the mounting part of the mounting tool becomes the pre-specified direction on the coordinates indicated in new X and Y axes.

6. The method of producing the three-dimensional shape data of the dental prosthesis as recited in claim 3, wherein the arithmetic process part has a compensation function for compensating a line to a smooth continuous line, which is drawn on the basis of the three-dimensional coordinates of the shape other than the engaging portion of the model of the dental prosthesis using Z axis as the reference.

7. The method of producing the three-dimensional shape data of the dental prosthesis as recited in claim 1, wherein the moving the XY table in the X and/or the Y axis directions in order to align the center axis T of the cylindrical part of the mounting tool with the Z axis step comprises, a mounting tool coordinate measuring step for measuring two-dimensional XY coordinates at plural points in even number by the measuring part of the three-dimensional measuring device, where the XY coordinates are positioned on an outer circumference of the cylindrical part of the mounting tool, a compensation value calculating step for calculating numerical total values of the X axis coordinate and Y axis coordinate of each point, dividing each total value by the number of the points to thereby obtain the XY coordinates of the center axis T of the mounting tool using the Z axis as the origin, calculating the difference in coordinate of the two-dimensional XY coordinates and the origin of the center axis T of the mounting tool, and thereby obtaining the compensation value of the center axis T of the mounting tool, and a position compensating step for moving the XY table in the X and/or Y axial directions on the basis of the compensation value to thereby align the center axis T of the cylindrical part of the mounting tool with the Z axis.

8. The method of producing the three-dimensional shape data of the dental prosthesis as recited in claim 7, wherein the mounting tool coordinate measuring step, the compensation value calculating step and the position compensating step are repeated, until the compensation value calculated by the compensation value calculating step becomes less than the minimum unit capable of moving the XY table.

9. A method of producing a three-dimensional shape data of a model of a dental prosthesis, wherein said data is subsequently used for cutting a block by an automatic cutting machine to create a dental prosthesis that has the same shape as that of the model of the dental prosthesis, wherein said method comprises the steps of:

providing a model of a dental prosthesis, said model having an engaging part on the jawbone side, said engaging part having a first cross sectional shape;

providing a three-dimensional measuring device, said three-dimensional measuring device comprising:

a XY table, said XY table being movable in both X axial and Y axial directions and rotatable about a Z axis, a placing table arranged on the XY table, a mounting tool fixed on an upper part of the placing table specifying a providing direction, said mounting tool comprising a cylindrical part, a mounting part on an upper face side of the cylindrical part, said mounting part having a second cross sectional shape for engaging with the engaging part of the model of the dental prosthesis, said mounting part being formed so as to position a prolonged line of a center axis T of the cylindrical part in the engaging part, and the placing part is formed and placed on said placing table so as to have the center axis T of the cylindrical part being vertical with respect to an upper surface of the XY table, the placing part is formed and placed on said placing table so as to have the center axis T of the cylindrical part being vertical with respect to the upper surface of the XY table, and the mounting part being aligned with the specified providing direction when the lower surface of the cylindrical part is placed on the placing table, and a measuring part for measuring the three-dimensional coordinates of the shape of a model mounted on the mounting tool, said measuring part including a laser sensor rotationally moving on one plane containing the Z axis at least around a desired point on the Z axis;

mounting the engaging part of said model of the dental prosthesis on the mounting part of said mounting tool;

mounting the mounting tool with the model of the dental prosthesis on the placing table;

moving the XY table in the X and/or the Y axis directions in order to align the center axis T of the cylindrical part of the mounting tool with the Z axis; and measuring said model of the dental prosthesis by rotating the XY table around the Z axis using the specified reference providing direction of the placing table and rotationally moving the laser sensor, to thereby produce three-dimensional data of the shape of the model of the dental prosthesis other than the engaging portion of the model.

10. The method of producing the three-dimensional shape data of the dental prosthesis as recited in claim 9, wherein the second cross sectional shape of the mounting part of the mounting tool has the shape where the completely same outside shape appears repeatedly for every 360 degree/n (n is a positive integer of 2 or more) around the prolonged line of the center axis T of the cylindrical part, and a figure formed by n time rotations is not circular.

11. The method of producing the three-dimensional shape data of the dental prosthesis as recited in claim 9, wherein said three-dimensional measuring device further includes an arithmetic process part, said arithmetic process part being used for arithmetic-processing of a measured value of the three-dimensional coordinates of the shape of the model measured by the measuring part of the three-dimensional measuring device.

12. The method of producing the three-dimensional shape data of the dental prosthesis as recited in claim 11, wherein the arithmetic process part changes the three-dimensional coordinates of the shape of the model other than the engaging part of the model using the Z axis as a reference to data for displaying an image on a computer.

13. The method of producing the three-dimensional shape data of the dental prosthesis as recited in claim 11, wherein the arithmetic process part changes the X and Y axes in the three dimensional coordinate of the shape of the model other than the engaging part of the model using Z axis as the reference, to the three-dimensional coordinates having new X and Y axes, where a point of the pre-specified direction of the mounting part of the mounting tool being orthogonally crossed with the Z axis is the origin of the new X and Y axes and the pre-specified direction of the mounting part of the mounting tool becomes the pre-specified direction on the coordinates indicated in new X and Y axes.

14. The method of producing the three-dimensional shape data of the dental prosthesis as recited in claim 11, wherein the arithmetic process part has a compensation function for compensating a line to a smooth continuous line, which is drawn on the basis of the three-dimensional coordinates of the shape other than the engaging part of the model of the dental prosthesis using Z axis as the reference.

15. The method of producing the three-dimensional shape data of the dental prosthesis as recited in claim 9, wherein the moving the XY table in the X and/or the Y axis directions in order to align the center axis T of the cylindrical part of the mounting tool with the Z axis step comprises, a mounting tool coordinate measuring step for measuring two-dimensional XY coordinates at plural points in even number by the measuring part of the three-dimensional measuring device, where the XY coordinates are positioned on an outer circumference of the cylindrical part of the mounting tool, a compensation value calculating step for calculating numerical total values of the X axis coordinate and Y axis coordinate of each point, dividing each total value by the number of the points to thereby obtain the XY coordinates of the center axis T of the mounting tool using the Z axis as the origin, calculating the difference in coordinate of the two-dimensional XY coordinates and the origin of the center axis T of the mounting tool, and thereby obtaining the compensation value of the center axis T of the mounting tool, and a position compensating step for moving the XY table in the X and/or Y axial directions on the basis of the compensation value to thereby align the center axis T of the cylindrical part of the mounting tool with the Z axis.

16. The method of producing the three-dimensional shape data of the dental prosthesis as recited in claim 15, wherein the mounting tool coordinate measuring step, the compensation value calculating step and the position compensating step are repeated, until the compensation value calculated by the compensation value calculating step becomes less than the minimum unit capable of moving the XY table.

* * * * *